United States Patent [19]
Rubenstein et al.

[11] 3,935,074
[45] Jan. 27, 1976

[54] ANTIBODY STERIC HINDRANCE IMMUNOASSAY WITH TWO ANTIBODIES

[75] Inventors: Kenneth Edward Rubenstein, Palo Alto; Richard K. Leute, Sunnyvale, both of Calif.

[73] Assignee: Syva Company, Palo Alto, Calif.

[22] Filed: Dec. 17, 1973

[21] Appl. No.: 425,376

[52] U.S. Cl............ 195/103.5 R; 23/230 B; 424/12; 424/1
[51] Int. Cl........................ G01n 31/00; C12k 1/04
[58] Field of Search............ 195/103.5 R; 23/230 B; 424/12

[56] References Cited
UNITED STATES PATENTS

| | | | |
|---|---|---|---|
| 3,839,153 | 10/1974 | Wilhelmus et al. | 195/103.5 R |
| 3,852,157 | 12/1974 | Rubenstein et al. | 195/103.5 R |

*Primary Examiner*—A. Louis Monacell
*Assistant Examiner*—C. A. Fan
*Attorney, Agent, or Firm*—Townsend and Townsend

[57] ABSTRACT

A novel immunoassay is provided, as well as particular reagents, for determining the presence of a ligand. A Reagent is employed having at least two epitopes, one of the epitopes being common with the ligand, and the other epitopes being foreign to the ligand. The two epitopes are positioned in the Reagent so that antibody bound to one of the epitopes sterically inhibits the binding of antibody to the second epitope.

In carrying out the assay, the sample, the Reagent, and antibodies to the two epitopes are combined. Because of the steric inhibition to the simultaneous binding of the two antibodies to the Reagent, the amount of antibody bound to the epitope of the Reagent foreign to the ligand will be related to the amount of ligand present in the assay medium. By analyzing directly or indirectly for the antibody bound to the epitope foreign to the ligand, and comparing the results to known standards, qualitative or quantitative determinations of the amount of ligand may be made. Various detector systems may be employed for determining the amount of antibody to the foreign epitope which is unbound or bound. These systems include stable free radicals, enzymes, radioactive labels, fluorescers, and the like.

24 Claims, No Drawings 3,935,074

ANTIBODY STERIC HINDRANCE IMMUNOASSAY WITH TWO ANTIBODIES

BACKGROUND OF THE INVENTION

1. Field of the Invention

Medical diagnosis is dependent to a great degree on the determination of the presence or absence of various compounds or their amounts in physiological fluids. Forensic medicine is also frequently concerned with the determination of the presence or absence of various physiologically active materials. Many systems have been developed to be able to accurately determine the presence and amounts of materials of interest.

One particular group of techniques is referred to as immunoassays. The immunoassays are dependent upon the recognition capability of a molecule, which may be referred to as a receptor, and is normally an antibody. Vertebrates have the capacity to produce molecules of protein which are able to distinguish a compound or group of compounds from other compounds which have similar or different structures. One immunoassay method, which has been available for a long period of time, is radioimmunoassay. Radioimmunoassay employs a molecule which has been tagged with a radioactive isotope. By combining an antibody to the ligand (ligand is the compound to be determined) with a small amount of ligand which has been tagged with a radioactive isotope and separating ligand bound to antibody from ligand which is unbound, the amount of radioactive ligand remaining in the supernatant solution will be related to the amount of ligand which was present in the original sample. Since this technique requires a separation into two phases, it will be referred to as a heterogeneous immunoassay technique.

Recently, two homogeneous immunoassay techniques have been developed by Syva Company, sold under the trademarks, FRAT, and EMIT. By homogeneous it is intended that after mixing the reagent, the assay does not require a separation step. The first homogeneous assay, the FRAT technique, uses a stable free radical tag, rather than a radioactive tag on the ligand. The ESR spectrum changes significantly in relation to the rate of tumbling of the free radical in solution. When the labeled ligand is bound to antibody, the peak height is substantially lower than when the labeled ligand freely tumbles in solution. Since the amount of labeled ligand bound to antibody will be related to the amount of ligand in solution, the peak height obtained with the assay solution can be related to known standards, and the concentration of the ligand determined.

The second homogeneous immunoassay involves an enzyme tag. The reagent employed has ligand bound to enzyme at a position, so that when antibody is bound to the ligand, the activity of the enzyme is substantially reduced. Thus, one can assay for enzyme activity in the assay solution, with the enzyme activity being related to the amount of ligand which was present in the unknown.

All of these techniques have been found to be highly sensitive, being able to detect concentrations of ligand at $10^{-6}M$ or below, and applicable to a wide variety of haptens and antigens. However, as is evident from the above discussion, a different detector molecule must be prepared for each ligand to be determined. While for many ligands no significant difficulty is encountered, with some ligands, substantial difficulty is encountered in preparing the detector molecule. It would be of great convenience if a single detector molecule could be prepared, which had the desired properties and could be used for detecting a wide range of ligands.

DESCRIPTION OF THE PRIOR ART

U.S. Pat. No. 3,709,868 is exemplary of a radioimmunoassay. U.S. Pat. No. 3,690,834 is exemplary of a spin immunoassay. U.S. Pat. No. 3,654,090 and German Auslegeschrift 2,223,385 are exemplary of enzyme immunoassays.

SUMMARY OF THE INVENTION

An assay technique is provided employing a Reagent having two epitopes, one common to a ligand to be determined and one foreign to the ligand. The two epitopes are spaced on the molecule, so that simultaneous binding to the same molecule of antibodies to the two epitopes is sterically inhibited.

In carrying out the assay, an unknown sample suspected of containing the ligand is combined with the Reagent and antibodies to the two epitopes in an aqueous medium at an appropriate pH. The distribution of antibody to the foreign epitope is then assayed by determining the amount of antibody either bound or unbound to the epitope, the amount being related to the amount of ligand in the unknown. Various assay techniques may be employed for determining the amount of bound or unbound antibody to the foreign epitope, such as radioimmunoassay, spin label immunoassay, homogeneous enzyme immunoassay, a fluorescent technique, and the like. A common detector molecule can be employed, and the double epitope Reagent varied. In this way, greater versatility and flexibility is achieved in preparing reagents in immunoassays.

DESCRIPTION OF THE SPECIFIC EMBODIMENTS

The assay of this invention is predicated on the ability to provide a molecule which has two different epitopes which are spatially situated in the molecule so that receptors to the molecule are sterically inhibited from being simultaneously bound to the two epitopes. The first epitope will be common to the compound to be assayed or ligand. The second epitope is involved with the group which is part of the detection scheme.

When an unknown suspected of containing a ligand is combined with the molecule having the two epitopes and receptor for the ligand, the amount of receptor bound to the molecule having two epitopes will be a function of the amount of ligand present. The amount of receptor which can bind to the second epitope will be a function of the remaining number of molecules having the two epitopes which are not bound to receptor for the first or ligand epitope. Therefore, by adding receptor for the second epitope and determining the amount that becomes bound or remains unbound, one can relate this value to the amount of ligand present in the unknown. Various detection schemes can be employed for determining the amount of bound or unbound receptor to the second epitope. These will normally employ chemical and/or physical methods for obtaining an electromagnetic signal.

DEFINITIONS

Whenever used in this specification, the following terms will have the meaning indicated.

Ligand — any molecule to which a receptor, normally an antibody, can be obtained or formed. Such molecule is normally antigenic or haptenic.

Epitope — that portion of a molecule which is specifically recognizable by a receptor, normally an antibody. It is also referred to as the determinant site.

Ligand Analog — a group having at least one epitope common to the ligand and normally differing from the ligand by removal of a hydrogen atom and replacement by a bond or linking group, so that the ligand analog is recognizable by the same receptor as is the ligand.

Reagent — a molecule having two different epitopes, one common with the ligand and the other, the detector epitope, which is associated with the assay method. The two epitopes are spatially juxtaposed, so as to inhibit simultaneous binding of receptors to the two epitopes.

Detectant — the means employed including any chemical reagents for determining the amount of bound or unbound detector epitope. There will be two primary means involved.

The first means has a detector ligand which gives a different electromagnetic signal, when subjected to electromagnetic radiation, when bound to receptor as compared to unbound, e.g. a fluorescing molecule.

The second means will employ a Detector Molecule which is capable of binding to receptor for the detector epitope. Determination of the amount of bound or unbound detector molecule permits determination of the amount of unbound or bound detector epitope.

Detector Ligand — the portion of the Reagent which contains the detector epitope. The group is bonded to the ligand analog by a bond or linking group. The same or substantially the same group will normally be present in the molecule employed as the detector molecule.

Assay

The subject assay is carried out in an aqueous medium at a moderate pH, generally close to the pH for optimum binding of the antibody to ligand, by combining a sample suspected of containing ligand, Reagent, antibodies to ligand (antiligand) and antibodies to detector ligand. (While the term "antibodies" will be used hereinafter, it is understood that antibodies is merely illustrative of receptors generally.) By employing a detectant, the amount of anti(detector ligand) which is bound and/or unbound to the detector ligand portion of the Reagent is determined. Because of the steric inhibition of simultaneous binding of antibodies to the ligand analog and detector ligand of the Reagent, the amount of bound and/or unbound anti(detector ligand) will be related to the amount of ligand which is present in the medium.

Where the Reagent has a plurality of epitopes common to the ligand and a pluralitty of epitopes common to the detector ligand, simultaneous binding of antibody to the two different epitopes can occur, except where the two different epitopes are sufficiently close together. Therefore, in referring to the steric inhibition of simultaneous binding of the two different antibodies, where a molecule has a plurality of epitopes common to the two different antibodies, the reference is to pairs of epitopes which provide the necessary steric inhibition, and not to the molecule as a whole.

The assay is concerned with available sites for binding of the anti(detector ligand) to Reagent. To the extent that all, or substantially all, of the Reagent present in the assay medium is bound to antiligand. the anti(detector ligand) will be precluded or substantially precluded from binding to Reagent. The more ligand present, the greater the amount of anti(detector ligand) which may bind to Reagent. Therefore, the amount of Reagent bound to anti(detector ligand) is related to the amount of ligand present in the assay medium.

In carrying out the assay, an aqueous medium will normally be employed. Other polar solvents may also be employed, usually oxygenated organic solvents of from 1 to 6, more usually from 1 to 4 carbon atoms, including alcohols, ketones, and the like. Usually, these co-solvents will be present in less than about 20 weight percent, more usually in less than about 10 weight percent.

The pH for the medium will usually be in the range of about 6 to 9, more usually in the range of about 7 to 8.5. Various buffers may be used to achieve the desired pH and maintain it during the determination. Illustrative buffers include borate, phosphate, carbonate, Tris, barbital, and the like. The particular buffer employed is not critical to this invention, but in particular assays, one buffer may be preferred over another.

Moderate temperatures are normally employed for carrying out the assay and usually constant temperatures during the period of the assay will be employed. The temperatures normally range from 15° to 50°C, more usually from about 20° to 40°C.

The concentrations of ligand which may be assayed for will vary from about $10^{-4}$ to $10^{-13}$M, more usually from about $10^{-6}$ to $10^{-11}$M. Whether the assay is qualitative, semi-quantitative or quantitative, the particular detection technique and the concentration of ligand of interest will normally determine the concentration of the other reagents. Normally, the concentration of Reagent will not exceed ten times and more usually will be equal to or less than the maximum concentration of interest, but will be no less than $10^{-4}$, more usually no less than $10^{-2}$ of the minimum concentration of interest. The antibody concentrations will normally not differ by more than about $10^2$, more usually by not more than about 10 from the concentration of Reagent.

The order of addition may vary widely. It is normally desirable to have the binding of one antibody go substantially to completion under the assay conditions, followed by the addition of the second antibody. Preferably, the unknown sample may be combined with the antiligand, followed by the addition of Reagent, followed by the addition of the anti(detector ligand). Depending on the particular assay technique, the detectant may now be employed. Alternatively, the ligand, Reagent and antiligand are combined, followed by the addition of anti(detector ligand).

In effect, one allows the amount of ligand present in the unknown to fill the available binding sites in accordance with the number of ligands present. This can be carried out in the absence of Reagent or in the presence of Reagent, where the Reagent will compete with the ligand present in the unknown for the available binding sites. Depending on the conditions employed, the amount of time allowed for the immunological reaction to occur, and the order of addition, there will be differing amounts of unbound Reagent. To the mixture is now added anti(detector ligand), which will combine with Reagent which is not bound to antiligand. By employing the appropriate detectant, one can analyze for the amount of bound or unbound anti(detector ligand), which amount is related to the amount of ligand present in the sample.

The times between the various additions and immunological reactions will vary widely, depending on the particular ligands involved, the mode of addition, the concentrations involved, the binding constants of the antibodies, and the like. Normally, times between additions may vary from a few seconds to many hours, usually not exceeding twelve hours, more usually not exceeding 6 hours. After adding each component to the assay mixture, different incubation periods before adding the next component or taking the measurement will be involved. Since the ultimate result will be dependent upon the results obtained with standards treated in substantially the same manner and, when possible, in the identical manner, the particular mode and periods of time are not critical, so long as the desired differentiation is obtained with varying concentrations of ligand and the results are reproducible.

Depending on the choice of the assay, the equipment employed and the concentration of ligand involved, assay volumes may be as small as about $1\mu l$, more usually at least $25\mu l$, and will usually not exceed 3ml, more usually not exceeding about 1ml.

With the exception of the electromagnetic radiation sensitive detector technique, all of the other detection techniques have been previously disclosed in the literature, a few references having been indicated previously. Therefore, as to those techniques which have been published, only a brief description of the method will be given.

In radioimmunoassay, the detectant involves a detector molecule which is a radioactive analog of the detector ligand. After combining the unknown, Reagent, the two antibodies and the radioactive analog, the bound radioactive analog may be separated from the unbound analog, by centrifugation, chromatography, or the like. One or both of the resulting fractions containing the bound and unbound components can then be assayed for the amount of radioactive analog which is present.

In the spin label technique, the detectant involves a detector molecule which is a spin labeled analog of the detector ligand. The assay mixture is taken up into an electron spin resonance cell and introduced into the cavity of an electron spin resonance spectrometer. The peak height may then be determined at one or more points in the spectrum.

In the enzyme technique, the detectant involves a detector molecule which is an enzyme labeled analog of the detector ligand. The necessary substrates are introduced into the assay mixture, and the enzyme activity determined in accordance with the particular enzyme. For example, with a dehydrogenase, the spectral change occurring as a result of the reduction of nicotinamide adenine dinucleotide may be determined after a fixed period of time for a specified period of time, for example, after 5 minutes from the addition for a period of 2 minutes.

In the electromagnetic sensitive detector technique, the detectant involves electromagnetic radiation, e.g. light, of an appropriate wavelength to be absorbed by the detector epitope. The sample is introduced into a spectrometer and absorption or emission of electromagnetic radiation is determined. With a fluorescing molecule, the sample is introduced into a fluorometer and irradiated with light at or near the absorption maximum of the fluorescer. The emission intensity is then determined. As will be discussed, the emission or absorption intensity will be a function of the amount of detector epitope bound to antibody.

MATERIALS

Ligand

The ligand may vary widely, normally having a molecular weight of at least 110, more usually at least 125, with a maximum molecular weight unlimited, although usually not exceeding 10 million. For the most part, the significant factor concerning a ligand is that a receptor can be made for the ligand or is available. Normally, receptors can be made for most organic compounds having a polar functionality. Compounds for which antibodies can be formed by bonding the compound to a compound having antigenic properties are referred to as haptens. Those compounds which elicit antibody formation without chemical modification are referred to as antigens. See Kabat et al, Experimental Immunochemistry, Charles C. Thomas, Springfield, Illinois, 1967.

Among ligands which are drugs, will be compounds which act as narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, $\alpha$-adrenergic blocking agents, antiadrenergic agents, ganglionic stimulating and blocking agents, neuromuscular agents, histamines, antihistamines, 5-hydroxytryptamine and antagonists, cardiovascular drugs, antiarrhythmic drugs, antihypertensive agents, vasodilator drugs, diuretics, pesticides (fungicides, antihelminthics, insecticides, ectoparasiticides, etc.), antimalarial drugs, antibiotics, antimetabolites, hormones, vitamins, sugars, thyroid and antithyroid drugs, corticosteroids, insulin, and oral hypoglycemic drugs, as well as other organic materials not normally considered drugs such as tumor cells, bacterial and viral proteins, toxins, blood proteins, and their metabolites.

(A drug is any chemical agent that affects living protoplasm. (Goodman & Gilman, The Pharmacological Basis of Therapeutics, 3rd Ed., Macmillan, New York (1965)). A narcotic is any agent that produces sleep as well as analgesia).

The non-polymeric compounds of interest will normally be of from about 125 to 2,000 molecular weight. These compounds involve a wide variety of compounds of varying structure, functionality, and physiological properties. The compounds may be acyclic, alicyclic or heterocyclic, both mono- and polycyclic. The heteroatoms involved include oxygen, nitrogen, sulfur, halogen (fluorine, chlorine, bromine and iodine) boron, phosphorous, metal cations of Groups 1A and 2A of the Periodic Chart, and the like.

The functionalities include alcohols, ethers, carboxylic acids, esters and amides, amines, (primary, secondary, tertiary and quaternary) halo, mercapto, nitrilo, and the like. Normally, the compounds will be composed solely of carbon, hydrogen, oxygen, sulfur, nitrogen, halogen, and phosphorous, particularly carbon, hydrogen, oxygen and nitrogen, and where salts are involved, the appropriate metal counterion or ammonium counterion.

Heterocyclic rings which are present include pyrrole, pyridine, piperidine, indole, thiazole, piperazine, pyran, coumarin pyrimidine, purine, triazine, imidazole, and the like.

Because of the wide variety of compounds which can be determined in accordance with the subject assay, the different groups will be broken down into various, frequently artificial, categories, either by the presence of a particular functionality or ring structure, or because of sharing a particular function or because of being recognized as a class.

The first class of compounds of interest are those having an amino group, either as a heterocyclic member, or as a functionality on an aliphatic chain. These compounds will normally be of from about 110 to 800 molecular weight, more usually of about 125 to 650 molecular weight.

The first group of compounds of interest are the alkaloids and the metabolites of those alkaloids which are ingested. The first group of important alkaloids are alkaloids of the morphine group. Included in this group are morphine, codeine, heroin, morphine glucuronide and the like.

The next group of alkaloids are the cocaine alkaloids, which include, particularly as metabolites, benzoyl ecgonine and ecgonine.

Another group of alkaloids are the cinchone alkaloids which include quinine.

The isoquinoline group of alkaloids includes mescaline.

The benzylisoquinoline alkaloids include papaverine.

The phthalide isoquinoline alkaloids include narcotine, narceine and cotarnine.

The indolopyridocoline alkaloids include yohimbine and reserpine.

The ergot alkaloids include ergotamine and lysergic acid.

Other groups of alkaloids include strychnine alkaloids, pyridine alkaloids, indole alkaloids, piperidine alkaloids, pyrrolizidine alkaloids, and the like.

The alkaloids of primary interest are those which come within the category of drugs of abuse, such as morphine, cocaine, mescaline, and lysergic acid, which may be analyzed for the compound or its metabolite, depending on the physiological fluid which is analyzed for its presence.

A number of synthetic drugs mimic the physiological properties, in part or in whole, of the naturally occurring drugs or abuse. Included among these drugs are methadone, meperidine, amphetamine, methamphetamine, glutethimide, diphenylhydantoin, and drugs which come within the category of benzdiazocycloheptanes, phenothiazines, and barbiturates.

Drugs of interest because of their physiological properties are those which are referred to as catecholamines. Among the catecholamines are epinephrine, ephredine, L-dopa and norepinephrine.

Another drug of interest is the tranquilizer Meprobamate.

Other compounds of interest are tetrahydrocannabinol, cannabinol, and derivatives thereof, primarily compounds derived from marijuana, synthetic modifications and metabolites thereof.

Another group of compounds of significant interest are the steroids. The steroids include estrogens, gestogens, androgens, adrenocortical hormones, bile acids, cardiotonic glycoids, algycones, saponins and sapogenins.

Another class of compounds are the vitamins, such as vitamin A, the B group, e.g., vitamin $B_1$ and $B_{12}$, E, K, and the like.

Another class of compounds are the sugars, both the mono- and polysaccharides, particularly di- and higher order polysaccharides.

Another class of compounds is the prostaglandins.

Another class of compounds is the amino acids, polypeptides and proteins. Polypeptides usually encompass from about 2 to 100 amino acid units (usually less than about 12,000 molecular weight). Larger polypeptides are arbitrarily called protein and are usually composed of from about 1 to 20 polypeptide chains. Poly(amino acid) will be used as generic to polypeptides and proteins. Of particular interest among amino acids are the iodosubstituted thyronines, e.g. thyroxine, (tetraiodothyronine) and triiodothyronine.

Another group of compounds are the antibiotics such as penicillin, actinomycin, chloromycetin, and the like.

Individual compounds of interest are serotonin, spermine and phenylpyruvic acid.

Finally, compounds which are pesticides, such as fungicides, insecticides, bactericides, and nematocides, may also be of interest for assaying.

REAGENT

The Reagent will be a molecule having two parts: ligand analog, including the linking group, and detector ligand.

While the linking group has been associated with the ligand analog, the linking group could be derived during synthesis of the Reagent from the precursor for the detector ligand. How Reagent is synthesized will depend on the groups involved in forming Reagent. It should be understood that including the linking group as part of the ligand analog is merely a matter of convenience for purposes of discussion.

In most cases, the ligand analog will have a hydrogen of the ligand replaced with a bond to a linking group. As for example, with morphine, the hydrogen of the phenolic hydroxyl can be replaced with a bond to the methylene of an acetyl group. The hydrogen may be replaced by a bond to a linking group which is joined to carbon, either aliphatic or aromatic, oxygen or nitrogen.

In some instances, an oxocarbonyl may serve as the linking site by modifying the oxocarbonyl to an oxime. In other instances, the hydroxyl of a carboxyl group may be replaced to form a linking group, by forming an ester or amide.

Additional alternatives include introducing functionalities, such as hydroxyl functionalities from which ethers can be formed, amino functionalities, from which diazo groups can be formed, and the like.

The significant factor for the ligand analog is that it has sufficient structural similarity to the ligand so as to be recognized by the antibody for the ligand. Because the manner of addition can be widely varied, the antibody binding constants for the ligand and the ligand analog may be different, but should not differ by more than a factor of $10^4$, preferably by not more than a factor of $10^2$.

For the most part, the ligand analog will have the same or substantially the same structure and charge distribution (spatial and polar organization) as the ligand for a significant, if not major, portion of the molecular surface. Since frequently, the linking site for a hapten will be the same in preparing the antigen for production of antibodies as used for linking to the detector ligand, the same portion of the ligand analog which provides the template for the antibody will be exposed by the ligand analog in the Reagent.

Because of the requirement for steric inhibition due to the presence of one antibody preventing the binding of another antibody to the Reagent, the linking group will normally be relatively short. Usually, the linking group will be substantially less than 25 A, more usually less than 20 A, and preferably less than 15 A. Normally, the linking group will be from about 1.5–10 A.

The linking group will normally be either a bond or a group of from 1 to 10 atoms, more usually from about 2 to 8 atoms, other than hydrogen. The linking group will normally be composed of carbon, hydrogen, oxygen, sulfur, phosphorous and nitrogen, usually having a nonoxocarbonyl group as part of the linking functionality. (Nonoxocarbonyl is intended to include the amino analogs thereof, e.g. imidate, amidine, etc.

In many molecules, the molecule may have a plurality of epitopes distant from one another. For example, polypeptides and proteins are known to have a number of different epitopes. When the detector ligand is bonded to a polypeptide ligand analog (in this case usually the linking group will have initially been bonded to the detector ligand) the detector ligand should be within the distances indicated above from an epitope to which an antibody is present in the assay medium. In effect, this molecule will have a plurality of Reagent portions, whereby antibody to the ligand epitope and antibody to the detector ligand are sterically inhibited from being simultaneously bound. For the purposes of this invention, such pairs of ligand analog epitope and detector ligand epitope are considered equivalent to the situation where a ligand analog has a single epitope.

While theoretically, with the exception of the electromagnetic sensitive detector assay, the detector ligand may be any ligand other than the ligand to be measured, as a practical matter the detector ligand will normally be a molecule of molecular weight in the range of about 125 to 1,200, more usually 125 to 800. Also, it will usually be preferred that the detector ligand will normally not be encountered in the media which are assayed. In addition, the detector ligand should have receptors available or allow for the formation of antibodies having high specificity. Another consideration is synthetic convenience, so that the detector ligand may be readily bonded to antigenic materials, the ligand analog, and the detector molecule. Finally, the detector ligand should be substantially free from interfering physical and chemical properties, such as non-specific binding, susceptibility to oxidation or reduction, susceptibility to chelation and the like. That is, the detector ligand should be free of functionalities which will result in interaction with the medium which would change the binding characteristics of the detector ligand with its antibody.

As already indicated, a ligand will normally have at least one polar functionality. For the detector ligand, two polar functionalities will usually be present and generally not more than about three polar functionalities, usually not more than about 30 polar functionalities, more usually not more than about four polar functionalities. By polar functionality is intended a functionality having from one to three heteroatoms, e.g. oxocarbonyl, nonoxocarbonyl, hydroxy, acetal, hemiacetal, nitro, amino, and the like. Included in the number of heterofunctionalities is the heterofunctionality employed in the linking group. Usually, the detector ligand will be cyclic, frequently polycyclic, having from one to five rings, and preferably having at least one ring which is aromatic. The detector ligand may be carbocyclic, heterocyclic, aromatic, or have all these groups.

As indicated, the requirements for the ligand are so general, that no particular structure or compound can be specified. In addition, different detector ligands may be of particular advantage with different ligands.

As previously mentioned, one of the advantages of the subject invention is that a single detectant can be employed in the detection of a wide variety of ligands. Thus, one can employ a single compound having a radioactive tracer for determining a wide variety of different ligands. In this manner, one need only store a single radioactive compound for carrying out a wide variety of assays. Since radioactive compounds have relatively short shelf lives, the advantage of using one single radioactive compound for assaying for a wide variety of ligands, is self evident.

With the enzyme assay and the spin label assay, there are numerous synthetic conveniences in having a single detectant. For example, with the spin label or stable free radical, one of the stable free radicals which is employed is the nitroxide free radical. The nitroxide compounds tend to be relatively water insoluble. If the ligand is also hydrophobic, some technique must be provided for enhancing the hydrophilicity of the resulting ligand-spin label conjugate. By contrast, in the subject invention, the detector ligand of choice can be hydrophilic. In this manner, the detector ligand will render the Reagent and detector molecule water soluble.

Similar considerations are involved in the enzyme process whereby efforts can be made to optimize the properties of a particular enzyme with respect to a particular ligand, which combination can then serve as a universal detector molecule for a wide variety of ligands.

In the case where light is the detectant, the detector ligand portion of the Reagent may be a fluorescing group. In choosing the particular fluorescer, a number of general considerations will come into play. The choice of fluorescer will, to a degree, be governed by the ligand. The fluorescer should have light absorption at higher wavelengths than the ligand or ligand-antibody complex. Since one is concerned with a change in the fluorescer emission spectrum as a result of its being bound or unbound to antifluorescer, the emission spectrum of the particular fluorescer compound should be sensitive to the environmental change produced by binding to antifluorescer.

Also, since proteins absorb at a wavelength of about 280, the fluorescer should have an absorption maximum above 300 and preferably above 400. The molar extinction coefficient should be greatly in excess of 10 l./mole-cm, preferably in excess of $10^3$ l./mole-cm and particularly preferred in excess of $10^5$ l./mole-cm. In addition, a fluorescer of choice will have a large Stokes shift. That is, there should be a substantial spread or difference in wavelengths between the longest wavelength absorption maximum of the fluorescer and the shortest wavelength emission maximum of the fluorescer. An additional consideration is that where physiological fluids are concerned, the fluorescer should have minimum non-specific binding to protein.

A number of different fluorescers are described in an article by Brand et al, Fluorescence Probes for Structure, Annual Review of Biochemistry, 41 843–868 (1972) and Stryer, Science, 162, 526 (1968).

One group of fluorescers having a number of the desirable properties described previously are the xanthene dyes, which include the fluoresceins derived from 3,6-dihydroxy-9-phenyl-xanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the napthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate. The naphthalene compounds are found to have some non-specific binding to protein, so that their use requires employment in an assay medium where the amount of protein is minimized.

DETECTANT

With the exception of the electromagnetic radiation sensitive detector ligand, the other techniques require the presence of a detector molecule.

In the case of radioimmunoassay, the detector ligand will differ from the ligand by the presence of a radioactive tracer, such as covalently bound tritium, carbon 14, or iodine (atomic weight 125). While other radioactive tracer elements could be used, these particular radioactive elements have found popularity because of synthetic convenience, reasonable shelf life, safety in handling, and the like.

For the spin labeled detector molecule, the detector ligand will be bonded by a linking group, previously described, to a stable free radical group, normally a cyclic nitroxide, disubstituted at the alpha carbon atoms with lower alkyl groups, usually methyl.

For the most part, the spin label compounds will have the following formula:

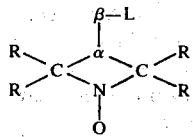

wherein R is a lower alkyl group of from 1 to 3 carbon atoms, usually methyl;

alpha is a divalent aliphatic group of from 1 to 3 carbon atoms having from 0 to 1 site of ethylenic unsaturation;

beta is a linking group or bond, wherein the linking group is of from 1 to 12 atoms other than hydrogen, usually of from 2 to 6 atoms other than hydrogen, normally having a nonoxocarbonyl group and composed solely of carbon, hydrogen, nitrogen and oxygen, and L is the ligand.

The nitroxide ring will normally have from 5 to 6 annular atoms.

The enzyme detector will have on the average at least about one detector ligand bonded to the enzyme, whereby when antibody is bound to the detector ligand, the enzymatic activity is substantially diminished. The average number of detector ligands per enzyme will normally be in the range of about 1 to 25, more usually in the range of about 2 to 20 and preferably in the range of about 1 to 12, usually not exceeding one detector ligand per 2,000 molecular weight of enzyme.

The enzymes of significant interest are the hydrolases, lyases and oxidoreductases. Enzymes of particular interest are lysozyme, malate dehydrogenase, glucose-6-phosphate dehydrogenase and amylase. Enzymes of choice have easy detection systems, e.g. spectrophotometric, have large turnover numbers, are relatively stable, and are not present in the materials to be analyzed or may be easily destroyed or removed prior to the assay.

EXPERIMENTAL

The following examples are offered by way of illustration, and not by way of limitation.

All temperatures are in centigrade unless otherwise indicated.

EXAMPLE I — Homogeneous Enzyme Immunoassay for Insulin

The following reagents were employed:
1. Serum containing insulin;
2. Carboxymethylmorphine conjugate to insulin, $2 \times 10^{-4}$M carboxymethylmorphine;
3. Antiinsulin, $1.08 \times 10^{-5}$M based on binding sites;
4. One weight percent bovine serum albumin in a buffer, which is 0.055M Tris-HCl, pH 7.8 at 30°, 0.003M $MgCl_2$, and $10^{-3}$M sodium azide;
5. Morphine conjugate to glucose-6-phosphate dehydrogenase having 11.5 haptens on the average per enzyme and a concentration of 0.5mg. per ml;
6. Antimorphine, $2.1 \times 10^{-4}$M based on binding sites;
7. Glucose-6-phosphate, Calbiochem, cat. no. 34676 as the disodium salt dihydrate, A grade, 67.2mg per ml in buffer; and
8. NAD, Sigma, Grade III from yeast, 58.8mg per ml in water at pH 5–6 employing sodium hydroxide.

The assay solution was prepared combining 100μl of serum, sufficient of the carboxymethylmorphine insulin conjugate to provide $2 \times 10^{-12}$ mole of carboxymethylmorphine conjugate (average of ≈ 11.5 morphine serum albumin buffer solution to bring the total volume to 550μl The assay mix was then incubated for 3 hours in a 37° water bath.

Solutions of glucose-6-phosphate dehydrogenase morphine conjugate (average of G2G11.5 morphine molecules per enzyme molecules) and antimorphine were combined to provide 400μl of solution 0.11 × $10^{-9}$M in enzyme and $2.5 \times 10^{-9}$M in antimorphine (based on binding sites). This solution was combined with the above solution and incubated for three hours at 37°.

At the end of this time, 25μl containing $5 \times 10^{-9}$ mole G6P and 25μl of $2 \times 10^{-9}$ mole NAD were added to the incubated mixture and an aliquot introduced at once into a spectrophotometer. A second aliquot was incubated at 37° for 2 hours and then introduced into the spectrophotometer. The enzyme activity for the sample immediately read and the sample read after two hours was determined by reading the value at 340nm. The difference between the two values is indicative of the rate of reaction of the enzyme or the enzymatic activity. Reaction concentrations less than $1 \times 10^{-8}$M of insulin gave detectable differences from a sample containing no insulin.

EXAMPLE II — Spin Label Immunoassay for Detection of Dinitro Aniline

The following reagents were employed:
1. Buffer — 0.013M sodium phosphate, pH 7.4, 0.13M NaCl, $10^{-4}$M thimerosal;
2. Antimorphine $2.1 \times 10^{-4}$M in binding sites;
3. N - (2',2',5',5'-tetramethylpyrrolidinyl-1'-oxyl) $O^3$-morphinoxyacetamide.
4. Antidinitroaniline;
5. 3-(2',4'-dinitroanilino)-2,2,5-tetramethylpyrrolidinyl-1-oxyl, $3.48 \times 10^{-5}$M in 5 percent methanol in water;
6. $N^5$-(2',4'-dinitrophenyl) $N^2$-($O^{3''}$-morphinoxyacetyl) lysine, $7.79 \times 10^{-5}$M in buffer.

Dinitrophenylmorphine, antidinitrophenyl and dinitrophenyllysine were combined to provide final concentrations of $5.6 \times 10^{-5}$M, $0.43 \times 10^{-5}$M in binding sites and $0.4 \times 10^{-5}$M respectively. To this mixture was then added a solution of antimorphine and morphine spin label which had been preincubated and provided a final concentration of antibody of $0.3 \times 10^{-5}$M in binding sites and $0.33 \times 10^{-5}$M in spin label. It was found that about 40 minutes was required before equilibrium was achieved at which time a reading was made. It was found that at the indicated concentration of the ligand, the spin label was completely free, which indicated that the dinitrophenylmorphine was completely excluded from the antidinitrophenyl. Therefore, at lower concentrations of the dinitrophenyllysine, various amounts of the spin label compound would be bound by antimorphine.

The above procedure was repeated, except that a system for the analysis of morphine was carried out. Dinitrophenylmorphine and antimorphine were combined in amounts to provide a final assay concentration of $0.825 \times 10^{-5}$M and $0.5 \times 10^{-5}$M respectively. The mixture was incubated for one-half hour. To the mixture was then added antidinitrophenyl and dinitrophenyl spin label in amounts sufficient to provide a final assay concentration of $0.14 \times 10^{-5}$M and $0.154 \times 10^{-5}$M respectively, the mixture having been preincubated. When $0.44 \times 10^{-5}$M morphine was included in the assay mixture, $0.0077 \times 10^{-5}$M of the dinitrophenyl spin label was mobilized. Therefore, the presence of morphine affected the amount of free spin label.

EXAMPLE III — Fluorescent Assay for Morphine

The reagents which were employed were as follows: FLUMO (fluorescein-morphine conjugate) was $3 \times 10^{-6}$M in water; antifluorescein, was $5.6 \times 10^{-6}$M in binding sites, in water, 0.05M phosphate, pH 8.0; antimorphine was $2 \times 10^{-4}$M in binding sites, 0.05M Tris-HCl, pH 8.0, in saline solution; buffer was Tris/saline 0.05M/1, pH 8.0. Opiate solutions had 1,000μg/ml per ml of codeine.

All of the determinations were made at a sensitivity setting of 4 on a Perkin-Elmer MPST Fluorometer. The solutions were mixed in order from left to right as set forth in the table. Excitation light was 460nm and the emitted light read was at 516nm, with a band width of 10nm.

The following table indicates the results.

TABLE I

| Cell No. | Fluorescein-Morphine Vol. μl | Anti-Fluorescein Vol. μl | Anti-Morphine Vol. μl | Codeine Vol. μul | Reading Signal Intensity | Reading Time min. |
|---|---|---|---|---|---|---|
| 2 | 5 | — | — | — | 62 | |
| 2 | 5 | 5 | — | — | 21 | |
| 2 | 5 | 5 | 5 | — | 25 | |
| | | | | | 26.5 | 5 |
| | | | | | 27.5 | 90 |
| 4 | — | — | — | — | 8 | |
| 4 | — | 5 | — | — | 3.5 | |
| 4 | — | 5 | 5 | — | 3.5 | |
| | | | | | 5 | 5 |
| | | | | | 5.5 | 90 |
| 3 | — | — | — | — | 1.5 | |
| 3 | 5 | — | — | — | 46 | |
| 3 | 5 | — | 5 | — | 35.5 | |
| | | | | | 35 | 5 |
| 3 | 5 | 5 | 5 | — | 23 | |
| | | | | | 22.5 | 5 |
| 3 | 5 | 5 | 5 | 5 | 20 | |
| | | | | | 16 | 90 |
| 1 | — | — | — | — | 11 | |
| 1 | — | — | 5 | — | 14.5 | |
| 1 | | | | | 14.5 | 5 |
| 1 | — | 5 | 5 | — | 5 | |
| 1 | — | 5 | 5 | 5 | 5.5 | |
| | | | | | 6 | 90 |

Where a reading is given but the absence of any material is indicated, only buffer was present in the cell. The reading times indicate the interval of time from the time of the first reading to the reading for the result which is reported, the first reading being made within as short an interval as possible of the mixing.

The following examples describe the preparation of reagents which were not commercially obtained and were employed in the prior assays.

EXAMPLE A — Preparation of $O^3$-(2,4-dinitrophenylmorphine)

Into a reaction vessel was introduced 475mg of dry morphine in 15ml of dry DMSO, followed by the addition of 71mg (56 weight percent) of sodium hydride. The mixture was stirred under nitrogen for approximately 1 hour, when the sodium hydride had been dissolved. To the mixture was then added 2,4-dinitrofluorobenzene (308mg) and the mixture stirred overnight. After distilling off the DMSO (45°, 0.02mm Hg), the residue was dissolved in 100ml of hot 0.1N aqueous hydrochloric acid and allowed to cool. Yellow crystals (500mg) were collected which softened at 180° and decomposed at 200°. A portion of the hydrochloride product (100mg) was dissolved in 5ml of hot water and 300μl, N sodium hydroxide added. Upon cooling, 85mg pale yellow crystals were obtained. m.p. 250°(d).

EXAMPLE B — Conjugation of Carboxymethylmorphine-Insulin

Into a reaction vessel was introduced 10.2mg of O$^3$-carboxymethylmorphine ($^{14}$C) dissolved in dry 200μl dimethylformamide (DMF) and 2.5mg dry triethylamine. The solution was stirred, cooled to 0°, and 4.1mg isobutylchloroformate added, whereupon the mixture was stirred for 1 hour at the same temperature.

To a solution of 60mg insulin in 4ml carbonate buffer, 0.1M, pH 9.2 was added the above solution at 0°. A precipitate formed which dissolved slowly, after 2 hours of stirring the reaction mixture.

No separation of unreacted carboxymethylmorphine from insulin was achieved by applying the mixture on a Sephadex column G-15 (K9/30) which had been equilibrated with PBS, pH 8.0, 0.1M. A column (K26/40) half filled with G-15 gave partial separation of the protein from the carboxymethylmorphine. Fractions 9–20 were combined to give 32ml of the solution. A slight precipitate was removed by addition of two drops of 2N sodium hydroxide.

The solution was acidified to pH 3.5 with 3N HCl and dialyzed overnight against 1.5 liters, 0.3 percent acetic acid. Radioactivity of the dialysate was 94 cpm/0.5ml, showing no conjugate.

Fractions 21–32 were combined and dialyzed against 1.1 liters 0.3 percent acetic acid. Radioactivity 1297 cpm/0.5ml.

EXAMPLE C — O$^3$-morphinoxyacetimidine derivative of Glucose-6-phosphate dehydrogenase Methyl O$^3$-(morphinoxyacetimidate) was prepared in accordance with the method described in application Ser. No. 358,757, filed May 9, 1973, which pertinent portion is incorporated herein by reference.

Into a reaction vessel was introduced $3.85 \times 10^{-8}$M of G-6-PDH (Beckman Microbics Operations) in an aqueous buffer 0.055M Tris, 0.003M MgCl$_2$, pH 8.5. To the mixture was added 118mg NADH and 68mg G-6-P, followed by addition of 75μl, 0.2M methyl O$^3$-(morphinoxyacetimidate). The mixture was stirred for 3 hours at room temperature and dialyzed against the above indicated buffer at pH 7.9. The dialysate was diluted to 8ml with the above buffer, pH 7.9.

EXAMPLE D — Preparation of Morphine-fluorescein Conjugate

Into a reaction vessel was introduced 68.8mg (0.2mmole) O$^3$-carboxymethylmorphine in 2ml DMF, the mixture cooled to −5° and 26μl (0.2mmole) isobutyl chloroformate added. The mixture was then stirred for 45 minutes. The resulting solution was then added slowly in 0.05ml portions to 36mg 4-aminofluorescein hydrochloride (Sigma isomer II·HCl) in 1ml butanol cooled in an ice bath. The mixture was allowed to stand 90 min. before workup.

The reaction mixture was streaked directly on a preparative thin layer chromatography plate and eluted with CHCl$_3$; MeOH; HOAc (75:50:10). After repeating the chromatography, the product was extracted from the silica gel with methanolic sodium hydroxide. The methanol was evaporated, water added, and the resulting precipitate was rinsed thoroughly. The product was redissolved in methanolic sodium hydroxide, water added, the methanol evaporated and the pH adjusted to 8.0 with HCl to provide a solution of the desired product.

It is evident from the prior results that by employing a reagent having a ligand analog and a detector ligand, numerous practical advantages can be achieved. First, one detector system can be used for a wide variety of ligands. By appropriate choice of the detector ligand, solubilization of the ligand can be enhanced and improved. Enhanced use of a single reagent which has a limited lift time, as in radioimmunoassay, can provide substantial economies in the utilization of the radioactive reagent. Economies in chemical synthesis can be achieved due to synthetic simplification. Besides the advantages of having a single reagent, there is the fact that a highly sensitive method is obtained for determining the presence, either qualitatively or quantitatively, of a wide variety of organic compounds with high specificity.

Although the foregoing invention has been described in some detail by way of illustration and example for purposes of clarity of understanding, it will be obvious that certain changes and modifications may be practiced within the scope of the appended claims.

We claim:

1. A method for determining the presence of a ligand in an unknown suspected of containing said ligand which comprises:

combining in an aqueous medium said unknown, antiligand, anti(detector ligand) and Reagent, wherein said Reagent has a pair of epitopes in close proximity so that simultaneous binding of receptors to said pair of epitopes is sterically inhibited, wherein one of said pair of epitopes is recognized by said antiligand and the other of said pair of epitopes is recognized by said anti(detector ligand);

determining by a detectant the amount of remaining unbound anti(detector ligand) or anti(detector ligand) bound to Reagent; and determining the presence of ligand by comparing said amount determined with said amount determined with a medium having a known amount of ligand.

2. A method according to claim 1, wherein said aqueous medium is buffered at a pH in the range of 6 to 9 and said determining is carried out at a temperature in the range of about 15° to 40°C.

3. A method according to claim 2, wherein said detectant includes a detector molecule having an epitope recognized by said anti(detector ligand) and a stable free radical group.

4. A method according to claim 3, wherein said stable free radical group is a cyclic nitroxide.

5. A method according to claim 2, wherein said detectant includes a detector molecule having an epitope recognized by said anti(detector ligand) and a radioactive atom.

6. A method according to claim 2, wherein said detectant includes a detector molecule having an epitope recognized by said anti(detector ligand) and an enzyme, wherein said activity of said enzyme is substantially reduced when said epitope recognized by said anti(detector ligand) is bound to antibody.

7. A method according to claim 6 wherein said enzyme is lysozyme, glucose-6-phosphate dehydrogenase, malate dehydrogenase, or amylase.

8. A method according to claim 2, wherein said ligand is a drug of molecular weight in the range of 125 to 2,000.

9. A method according to claim 8, wherein said ligand is an alkaloid.

10. A method according to claim 8, wherein said ligand is a catecholamine.

11. A method according to claim 8, wherein said ligand is an opiate.

12. A method according to claim 8, wherein said ligand is a cardiac glycoside.

13. A method according to claim 8, wherein said ligand is a vitamin.

14. A method according to claim 8, wherein said ligand is an iodo substituted thyronine.

15. A method according to claim 8, wherein said ligand is a steroid.

16. A method according to claim 2, wherein said ligand is an amino acid or poly(amino acid) of from 2 to 100 amino acid units.

17. A method for determining the presence of a ligand in an unknown suspected of containing said ligand which comprises:

combining in an aqueous medium buffered at a pH in the range of 6 to 9, said unknown, Reagent and antiligand, wherein said Reagent has a pair of epitopes in close proximity, so that simultaneous binding of antibodies to said pair of epitopes is sterically inhibited, wherein one of said pair of epitopes is recognized by said antiligand and the other of said pair of epitopes is recognized by an anti(detector ligand);

incubating for sufficient time for a steady state to be obtained;

adding anti(detector ligand); and determining by a detectant at a temperature in the range of 15° to 40°C, the amount of remaining unbound anti(detector ligand) or anti(detector ligand) bound to Reagent; and determining the presence of ligand by comparing said amount determined with said amount determined with a medium having a known amount of ligand.

18. A method according to claim 17, wherein said detectant includes a detector molecule having an epitope recognized by said anti(detector ligand) and a stable free radical group.

19. A method according to claim 17, wherein said detectant includes a detector molecule having an epitope recognized by said anti(detector ligand) and a radioactive atom.

20. A method according to claim 17, wherein said detectant includes a detector molecule having an epitope recognized by said anti(detector ligand) and an enzyme whose activity is substantially reduced when said epitope is bound to said anti(detector ligand).

21. A method for determining the presence of a ligand in an unknown suspected of containing said ligand which comprises:

combining in an aqueous medium buffered at a pH in the range of 6 to 9, said unknown and antiligand;

incubating said aqueous medium for sufficient time to obtain a steady state;

adding Reagent to said aqueous medium, wherein said Reagent has a pair of epitopes in close proximity, so that simultaneous binding of antibodies to said pair of epitopes is sterically inhibited, wherein one of said pair of epitopes is recognized by said antiligand and the other of said pair of epitopes is recognized by an anti(detector ligand);

incubating for a sufficient time to establish a steady state;

adding anti(detector ligand);

determining by means of a detectant the amount of remaining unbound anti(detector ligand) or anti(detector ligand) bound to Reagent; and determining the presence of ligand by comparing said amount determined with a medium having a known amount of ligand.

22. A method according to claim 21, wherein said detectant includes a detector molecule having an antibody recognized by said anti(detector ligand) and a stable free radical group.

23. A method according to claim 21, wherein said detectant includes a detector molecule having an epitope recognized by said anti(detector ligand) and a radioactive atom.

24. A method according to claim 21, wherein said detectant includes a detector molecule having an epitope recognized by said anti(detector ligand) and an enzyme whose activity is substantially reduced when said epitope is bound to said anti(detector ligand).

* * * * *

UNITED STATES PATENT OFFICE
CERTIFICATE OF CORRECTION

PATENT NO. : 3,935,074

DATED : January 27, 1976

INVENTOR(S) : KENNETH EDWARD RUBENSTEIN, RICHARD K. LEUTE

It is certified that error appears in the above-identified patent and that said Letters Patent are hereby corrected as shown below:

Column 12, line 43. After morphine, insert -- , --.

Column 12, line 43. After morphine, delete "conjugate (average of ≈11.5 morphine" and add --0.8μl of antiinsulin and 1% bovine--.

Column 12, line 48. Delete "G2G" and add --∼--.

Signed and Sealed this

Tenth Day of August 1976

[SEAL]

Attest:

RUTH C. MASON  
Attesting Officer

C. MARSHALL DANN  
Commissioner of Patents and Trademarks